(12) United States Patent
McDonald et al.

(10) Patent No.: US 11,173,256 B2
(45) Date of Patent: Nov. 16, 2021

(54) INJECTION DEVICE AND METHOD

(71) Applicants: Michael B. McDonald, Cordova, TN (US); Shalaka V. Bapat, New York, NY (US)

(72) Inventors: Michael B. McDonald, Cordova, TN (US); Shalaka V. Bapat, New York, NY (US)

( * ) Notice: Subject to any disclaimer, the term of this patent is extended or adjusted under 35 U.S.C. 154(b) by 0 days.

(21) Appl. No.: 17/357,043

(22) Filed: Jun. 24, 2021

(65) Prior Publication Data

US 2021/0316085 A1 Oct. 14, 2021

Related U.S. Application Data

(62) Division of application No. 17/261,793, filed as application No. PCT/US2020/020391 on Feb. 8, 2020, now Pat. No. 11,058,829.

(60) Provisional application No. 62/875,181, filed on Jul. 17, 2019, provisional application No. 62/812,532,
(Continued)

(51) Int. Cl.
| | |
|---|---|
| *A61M 5/32* | (2006.01) |
| *A61B 17/34* | (2006.01) |
| *A61M 5/00* | (2006.01) |
| *A61M 5/315* | (2006.01) |
| *A61M 39/06* | (2006.01) |
| *A61M 39/08* | (2006.01) |

(Continued)

(52) U.S. Cl.
CPC ....... *A61M 5/3295* (2013.01); *A61B 17/3468* (2013.01); *A61M 5/007* (2013.01); *A61M 5/31501* (2013.01); *A61M 39/06* (2013.01); *A61M 39/08* (2013.01); *A61B 2017/00247* (2013.01); *A61M 2025/0087* (2013.01); *A61M 2039/062* (2013.01); *A61M 2039/082* (2013.01)

(58) Field of Classification Search
CPC ................ A61M 5/3295; A61M 5/007; A61M 5/31501; A61M 39/08; A61M 39/06; A61M 2025/0087; A61M 2039/062; A61M 2039/082; A61B 2017/00247
See application file for complete search history.

(56) References Cited

U.S. PATENT DOCUMENTS

| | | | |
|---|---|---|---|
| 4,935,009 A | 6/1990 | Caldwell et al. | |
| 5,405,376 A * | 4/1995 | Mulier | A61M 25/0069 604/131 |
| 5,640,955 A | 6/1997 | Ockuly et al. | |

(Continued)

OTHER PUBLICATIONS

Written Opinion of the International Searching Authority in International Application PCT/US2020/020391 dated Jun. 9, 2020, 8 pages.

*Primary Examiner* — Amber R Stiles
(74) *Attorney, Agent, or Firm* — Jonathan Pierce; Pierre Campanac; Porter Hedges LLP

(57) ABSTRACT

An injection device is used for "tattooing" markers inside the heart of a patient at specific locations. Placement within the heart of markers, such as points marked with a radiopaque dye, may reduce the use of x-ray dye and echocardiography, may allow a quicker cardiac procedure, and thus may improve the procedure outcome for the patient. Alternatively or additionally to cardiac marking with a radiopaque dye, cardiac tissue fibrosis, cardiac tissue contraction, and/or cardiac tissue stiffening (or hardening) can be promoted at specific locations by delivering a suitable substance.

23 Claims, 6 Drawing Sheets

Related U.S. Application Data filed on Mar. 1, 2019, provisional application No. 62/903,044, filed on Sep. 20, 2019.

(51) Int. Cl.
*A61B 17/00* (2006.01)
*A61M 25/00* (2006.01)

(56) References Cited

U.S. PATENT DOCUMENTS

| | | | |
|---|---|---|---|
| 2002/0072717 A1* | 6/2002 | Mueller | A61B 17/3207 604/212 |
| 2002/0095124 A1* | 7/2002 | Palasis | A61B 17/32037 604/272 |
| 2002/0103110 A1* | 8/2002 | Spitzer | A61K 31/19 514/1 |
| 2004/0191225 A1 | 9/2004 | Dinsmore et al. | |
| 2005/0209699 A1* | 9/2005 | Slivka | A61L 27/227 623/17.16 |
| 2008/0160062 A1* | 7/2008 | Richard | A61L 31/048 424/423 |
| 2010/0160720 A1 | 6/2010 | Eby | |
| 2011/0028837 A1* | 2/2011 | Byrd | A61B 5/0044 600/433 |
| 2011/0087207 A1* | 4/2011 | Vogel | A61L 24/0015 606/27 |
| 2011/0236432 A1 | 9/2011 | Majd et al. | |
| 2014/0005533 A1 | 1/2014 | Grasruck et al. | |
| 2015/0202361 A1 | 7/2015 | Burns et al. | |
| 2015/0257877 A1 | 9/2015 | Hernandez | |
| 2017/0000609 A1 | 1/2017 | Gross et al. | |
| 2017/0189113 A1 | 7/2017 | Urbanski et al. | |
| 2018/0017577 A1 | 1/2018 | Franco | |
| 2019/0008557 A1 | 1/2019 | Lenker et al. | |
| 2019/0015002 A1 | 1/2019 | Fischell et al. | |

* cited by examiner

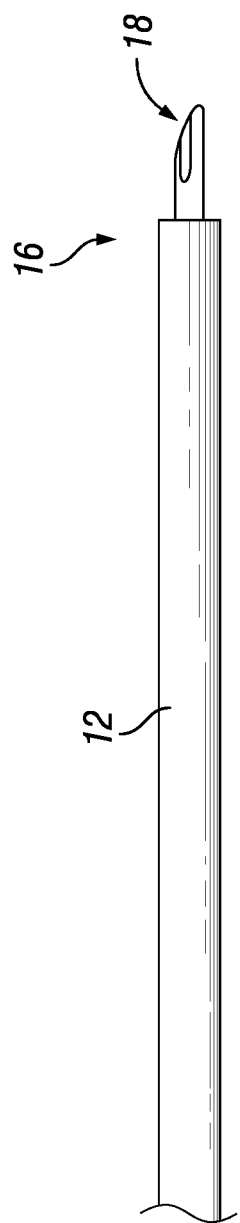
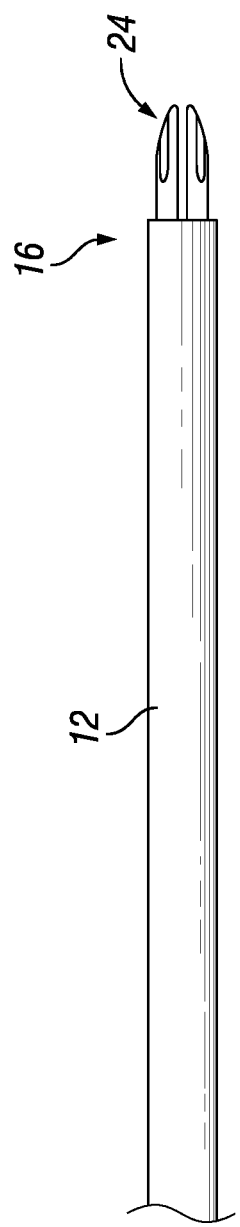

INJECTION DEVICE AND METHOD

CROSS-REFERENCE TO RELATED APPLICATIONS

This application is a divisional application of application Ser. No. 17/261,793 filed on Jan. 20, 2021, now U.S. Pat. No. 11,058,829, which is a national stage entry of international application serial no. PCT/US2020/020391 filed on Feb. 28, 2020, which claims the benefit of priority to provisional applications Ser. Nos. 62/903,044 filed on Sep. 20, 2019, 62/875,181 filed on Jul. 17, 2019, and 62/812,532 filed on Mar. 1, 2019. All the priority applications are included herein by reference for all and any purposes.

BACKGROUND

This disclosure relates generally to devices and methods for injecting a substance inside a tissue of a patient, for example, inside cardiac tissue, at specific locations. The substance may serve as a marker, or may induce a change in the tissue, or both. In some particular aspects, this disclosure relates to devices and methods for facilitating the placement and anchoring of implants in a patient. In some particular aspects, this disclosure relates to devices and methods for internal cardiac annuloplasty.

The field of structural heart procedures is the fastest-growing field in cardiac care. For example, a common structural heart procedure involves the placement inside the heart of a patient and the anchoring to the cardiac tissue of a cardiac valve anchor, an artificial cardiac valve, or another device related to cardiac valves.

The success of many structural heart procedures is dependent on knowing exact positions or landmarks within the heart. For example, a slightly misplaced cardiac valve or other device can be very compromising to the patient.

Structural heart procedures are presently very reliant on x-ray, x-ray dye, and echocardiography to help practitioners safely perform the structural heart procedures. Such use of x-ray, x-ray dye, and echocardiography results in long procedures that may pose a risk to the patients.

Further, the strength of the cardiac tissue in some areas of the heart may not be adequate to hold the cardiac valve anchors, and these anchors, if placed in these areas, may detach from the heart tissue not long after their implantation.

Also, mitral valve and tricuspid valve regurgitation (or leakage) accounts for, or contributes to, a significant amount of the congestive heart failure in the world. When the valve regurgitation is secondary to cardiac function and not from a primary abnormality of the valve leaflets, the usual cause is from dilatation of the valve's annulus. The annulus is essentially the backbone of the valve. As the annulus is expanded in congestive heart failure, the valve leaflets are pulled farther apart, resulting in more regurgitation and subsequently more congestive heart failure.

Presently in structural cardiology and cardiac surgery, there are multiple implantable devices to reduce the size of an expanded valve annulus.

There is a continuing need in the art for injecting a substance inside a tissue of a patient, for example, inside cardiac tissue, at specific locations.

BRIEF SUMMARY OF THE DISCLOSURE

The disclosure describes a surgical device that is usable for injecting a substance into the tissue of a patient, for example, heart tissue. In some embodiments, the surgical device may be for the placement and optionally the anchoring of an implant in the heart of a patient. In some embodiments, the surgical device may be for creating a cardiac annuloplasty ring chemically, the annuloplasty ring being at least partially embedded in the heart tissue.

The surgical device may comprise an injector device. The injector device may include a mechanism to hinder the flow of the fluid to be injected between successive ejections. In some embodiments, the mechanism to hinder the flow of the fluid to be injected between successive ejections may comprise a valve. In some embodiments, the mechanism to hinder the flow of the fluid to be injected between successive ejections may comprise a trigger capable of releasing a ratchet mechanism used to lock the position of a plunger. In some embodiments, the mechanism to hinder the flow of the fluid to be injected between successive ejections may comprise both a valve and a trigger capable of releasing a ratchet mechanism used to lock the position of a plunger. The injector device may further include a barrel for containing the fluid to be injected. The injector device may further include a plunger for applying pressure to the fluid being injected. The plunger may be slidable inside the barrel. The injector device may further include a rod. The rod may be connected to the plunger. The rod may be extending from the barrel.

In some embodiments, the injector device may contain a marking dye capable of being seen by x-ray or echocardiography. For example, the marking dye may be iodine-based and/or the marking dye may contain submicron tungsten. In some embodiments, the injector device may contain a substance capable of inducing fibrotic tissue changes. For example, the substance may be an irritant, the substance may be a fibroblast growth factor, and/or the substance may be cyanoacrylate. In some embodiments, the injector device may contain a liquid compound that is capable of solidifying and/or a substance like ethiodized oil. For example, the liquid compound may be cyanoacrylate. In some embodiments, the injector device may contain a combination of two or more of a marking dye capable of being seen by x-ray or echocardiography, a substance capable of inducing fibrotic tissue changes, and a liquid compound that is capable of solidifying.

The surgical device may comprise a tube having a proximal end and a distal end. The proximal end may be connected to the injector device. The tube may have a dual lumen. One of the lumens may provide passage to a form of energy, such as a laser beam.

The surgical device may comprise one or more needles. The one or more needles may protrude from the distal end of the tube. The distal end of the tube may be sealed around the one or more needles. On some embodiments, a plurality of needles may protrude from the distal end of the tube.

The surgical device may comprise an outer catheter. The outer catheter may have a bore sized to allow insertion and movement of the tube. The outer catheter may include a hemostatic valve positioned at a proximal end of the outer catheter. The hemostatic valve may be configured to allow insertion and movement of the tube. The outer catheter further may include a side port. The side port may be closable with a valve. The outer catheter may be a steerable guide catheter that can deflect a distal segment in four quadrants.

The disclosure also describes a method for placement and optionally anchoring of a replacement implant in the heart of a patient.

The method may comprise the step of accessing the heart of the patient with a surgical device as described hereinabove.

The method may comprise the step of injecting, with the surgical device, a controlled amount of a marking dye below the cardiac surface. Additionally or alternatively, the method may comprise the step of injecting, with the surgical device, a substance capable of inducing fibrotic tissue changes. If both a marking dye and a substance capable of inducing fibrotic tissue changes are injected, the marking dye and the substance capable of inducing fibrotic tissue changes can be injected simultaneously (e.g., as a mixture), or consecutively.

In some embodiments, the method may comprise the step of delivering a form of energy through the device for inducing fibrotic tissue changes.

The disclosure also describes a method for creating a cardiac annuloplasty ring chemically. The annuloplasty ring may be at least partially embedded in heart tissue. The method may be used for preventing and treating congestive heart failure.

The method may comprise the step of accessing the heart of the patient with a surgical device as described hereinabove.

The method may comprise the step of injecting, with the surgical device, a liquid compound that is capable of solidifying below the cardiac surface. Solidification of the compound may cause the hardening of the heart tissue in the area of injection. The preferred locations of injection of the liquid compound inside the tissue may be around the annulus of the mitral valve, around the annulus of the tricuspid valve, or around both annuli.

In some embodiments, the method may comprise fixing the annulus of the mitral and/or tricuspid valve at its present size to prevent future enlargement.

In some embodiments, the method may comprise constricting the annulus of the mitral and/or tricuspid valve and fixing the annulus of the mitral and/or tricuspid valve at a new, reduced size. Constricting the annulus of the mitral and/or tricuspid valve may be performed with a constriction catheter that can be positioned in the coronary sinus, for example, with the aid of a guidewire.

BRIEF DESCRIPTION OF THE DRAWINGS

For a more detailed description of the embodiments of the disclosure, reference will now be made to the accompanying drawings, wherein:

FIG. 2 is a perspective view of the distal portion of the injection catheter shown in FIG. 1, FIG. 3 is a perspective view of a distal portion of an injection catheter including a plurality of short needles;

DETAILED DESCRIPTION

It is to be understood that the following disclosure describes several exemplary embodiments for implementing different features, structures, or functions of the invention. Exemplary embodiments of components, arrangements, and configurations are described below to simplify the disclosure; however, these exemplary embodiments are provided merely as examples and are not intended to limit the scope of the invention.

The methods described herein may essentially result in "tattooing" markers inside the heart at specific locations. The markers may facilitate many cardiac procedures. Marking the location of internal cardiac structures can have an important impact on the success of heart procedures, such as the positioning of cardiac valves. Placement within the heart of markers, such as points marked with a radiopaque dye, would reduce the use of x-ray dye and echocardiography. These markers should allow a quicker cardiac procedure and improve the procedure outcome for the patient.

Alternatively or additionally to cardiac marking, the methods described herein may essentially result in promoting cardiac tissue fibrosis, cardiac tissue contraction, and/or cardiac tissue stiffening (or hardening) at specific locations by delivering a suitable substance.

Figure 1:
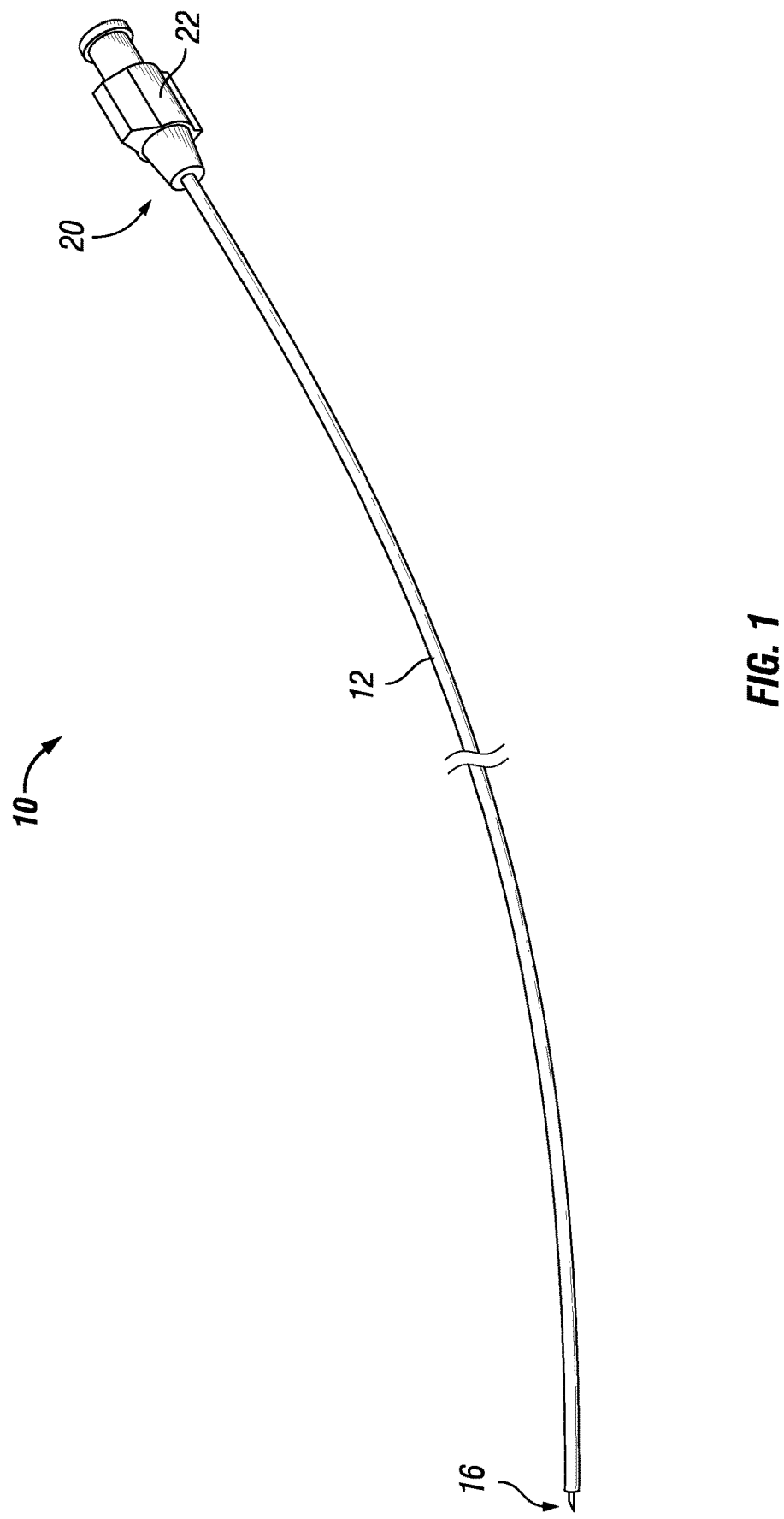
FIG. 1 is a perspective view of an injection catheter usable for injecting a fluid in the tissue of a patient.

FIG. 1 illustrates an injection catheter 10, which may be used for injecting a fluid in the tissue of a patient. For example, the injection catheter may be used for delivering a marker, such as a radiographic marker, inside the heart or other organ or tissue of a patient and/or for delivering a substance capable of inducing cardiac tissue fibrosis, cardiac tissue contraction, and/or cardiac tissue stiffening at specific locations.

The injection catheter 10 includes a polyimide or similar substance polymer tube 12. The proximal end 20 of the tube 12 has a conventional catheter connector. This connector can be coupled with tubing to the injector device 22. The distal end 16 is used to deliver fluid, for example, inside the heart of a patient.

Several different designs are possible for the injector device 22. For example, a simple device resembling a chalking gun may be employed. This injector device 22 would only eject a trace amount of fluid. For example, the injector device may include a barrel for containing the fluid to be injected, a plunger slidable inside the barrel for applying pressure to the fluid being injected, and a rod connected to the plunger and extending from the barrel. The rod may include a mechanism to hinder the flow of the fluid to be injected between successive ejections, such as a trigger capable of releasing a ratchet mechanism used to lock the plunger position. Alternatively, a fluid valve, such as 3-way stopcock and small syringe could also be used for ejection of very small amounts of fluid.

The marking dye can be any fluid that can be seen by x-ray or echocardiography. For example, the marking dye may be radiopaque. The x-ray dye used to mark the cardiac surface may be a known iodine-based x-ray dye. For example, one option is to use ethiodized oil. Preferably, but not necessarily, the iodine-based x-ray dye may not leave a permanent mark. Another option may be to use an x-ray dye that contains fluid and a substance of high radiographic density; submicron tungsten and/or tantalum may be an example of such substance. The x-ray dyes that contain submicron tungsten and/or tantalum may leave a permanent mark.

The substance capable of inducing tissue changes in the injected area may vary. For example, the substance may consist of an irritant that induces fibrotic tissue changes. In another example, the substance may consist of a fibroblast growth factor. Other known substances capable of inducing tissue changes may also be used.

In some embodiment, the fluid to be injected in the tissue includes a mixture of a marker, such as a radiographic marker, and a substance capable of inducing tissue changes.

FIG. 2 illustrates the distal portion of the injection catheter 10. The distal end 16 of the tube 12 includes a single short needle 18 (or other equivalent types of ejection port) that slightly protrudes from the distal end 16 of the tube 12. The distal end 16 of the tube is sealed around this needle/port so as to allow fluid only to exit the tube 12 through the needle/port.

FIG. 3 illustrates the distal portion of the injection catheter 10 in accordance with an alternative embodiment. The distal end 16 of the tube 12 includes a plurality 24 of short needles (or other equivalent types of ejection ports) that slightly protrude from the distal end 16 of the tube 12. Again, the distal end 16 of the tube is sealed around these needles/ports so as to allow fluid only to exit the tube 12 through the needles/ports.

While FIGS. 2 and 3 illustrate a distal end 16 of an injection catheter 10 that is round, in other embodiments, the shape is not so limited. For example, the shape of the distal end 16 may be oval, or even a slight crescent.

Figure 4:
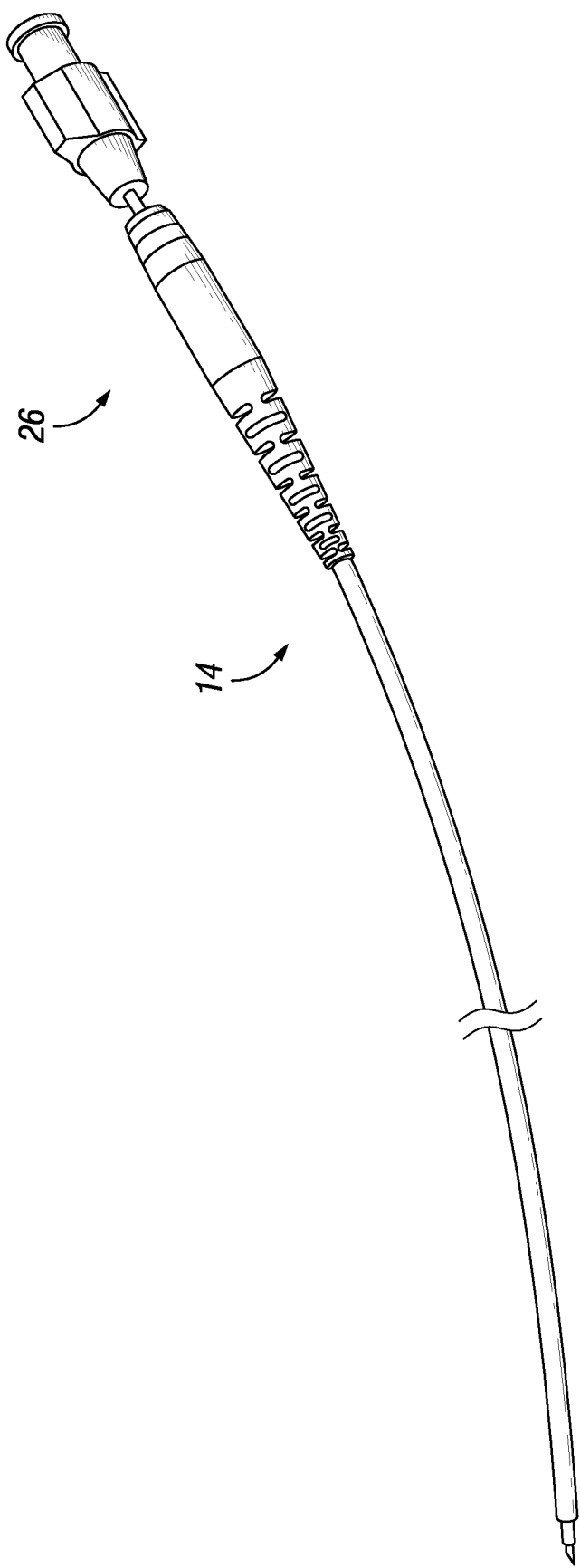
FIG. 4 is a perspective view of the injection catheter shown in FIG. 1, illustrated inside an outer catheter.

FIG. 4 illustrates an injection device comprising the injection catheter 10 inside an outer catheter 14, for example, an existing cardiac guide catheter.

The tube 12 has a diameter that fits inside the outer catheter 14 such that the injection catheter 10 can be freely moved inside the guide catheter 14. Optionally, the outer catheter 14 includes a hemostatic type valve 26 at the proximal end that still allows insertion and movement of the injection catheter 10. Flushing fluid can be used to prevent clotting within the injection device.

Optionally, the outer catheter 14 may be a steerable guide catheter that can deflect the distal segment in all four quadrants (medial and lateral, anterior, and posterior). For example, the diameter of the outer catheter 14 may be up to 24 in the French gauge system. Indeed, a larger bore may be well suited for the steerable function and for accommodating an injection catheter 10 of sufficient size.

Figure 5:
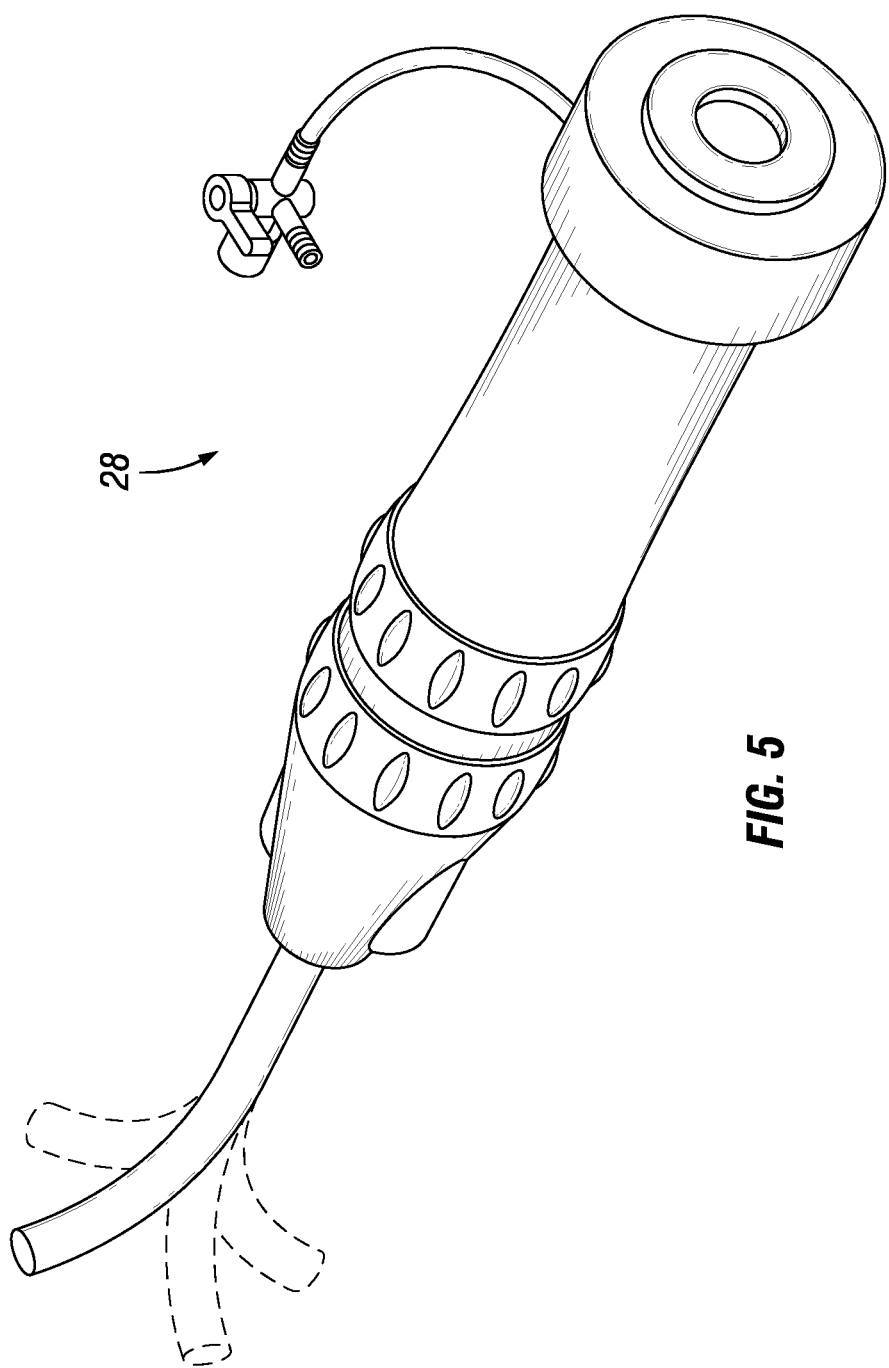
FIG. 5 illustrates a proximal portion of an outer catheter that is a guide catheter.

FIG. 5 illustrates the proximal portion of the outer catheter 14 in accordance with an alternative embodiment. The proximal end of the outer catheter 14 may be connected to a side port 28 for pressure monitoring as well as fluid flush. For example, the side port 28 may include a Tuohy valve.

In alternative embodiments not illustrated in FIGS. 1-5, the injection device may provide a passage for a laser beam or other form of energy that may be used to induce fibrotic changes as well as shrinkage to the treated tissue. The passage may be implemented with an injection catheter 10 having a dual lumen. One of the lumens can be used for the passage of the laser beam or the other form of energy. The other of the lumens may be used for the delivery of the marking dye or other substance.

For example, the injection device, including the outer catheter 14 and the injection catheter 10, may facilitate the placement and anchoring of a replacement implant of the native mitral valve or tricuspid valve. In such cases, venous access is typically obtained. If the mitral valve is replaced, trans-septal access may be obtained. Then, a guidewire is advanced to the desired position.

In an example use, the outer catheter 14, such as a cardiac guide catheter with a Tuohy valve connected to the proximal end, is advanced over the guidewire to the desired area of the heart to mark. The guidewire is then removed. The location of the distal end of the outer catheter 14 can be confirmed by injections of x-ray dye through the outer catheter 14 and/or with the use of transesophageal echocardiography. When the distal tip of the outer catheter 14 is in the proper position, the Tuohy valve is opened, and the injection catheter 10 is advanced inside the outer catheter 14. Before the injection catheter 10 exits the outer catheter 14, the distal position of the outer catheter tip can be confirmed with a dye injection through the outer catheter (as well as using transesophageal echocardiography to confirm the position of the distal tip). At this point, the injection catheter 10 is advanced slightly out of the guiding catheter 14 against the cardiac tissue. When stable placement against the cardiac tissue is confirmed, a very small amount of x-ray dye is injected or dotted just below the cardiac surface. If needed, several injections of dye can be used in the same area to produce a satisfactory radiographic marker. The same outer catheter 14 or an outer catheter of a different configuration may be used to place markers at nearby desired positions. After the desired radiographic markers are in place, the outer catheter 14 and injection catheter 10 are withdrawn. The intended structural heart procedure may then continue.

Another example use further involves the injection of a substance capable of changing tissues. As previously mentioned, the injection device, including the outer catheter 14 and the injection catheter 10, is first advanced to the atrial side of either the tricuspid valve or the mitral valve by x-ray and echocardiographic guidance. Once the position above the annulus of the native valve is confirmed, the outer catheter 14 can be advanced to the cardiac tissue surface or just above. The position of the outer catheter 14 against the cardiac tissue is confirmed by the pressure wave dampening. At this point, the injection catheter 10 is pushed against the surface to engage the needle/needles or other type of injection port slightly into the cardiac tissue. The tissue is then injected with the mix of marker dye and the substance capable of promoting tissue change. This step is then repeated around the annulus of the native valve. In some cases, the injected area will match the footprint of the implant device to be implanted. After completion of the tissue marking and tissue treatment, the injection device is removed. After an appropriate waiting period (which will typically be a few months), the patient can be brought back for the artificial valve implantation.

Accordingly, the injection device described herein may improve outcomes of structural heart procedures, and may result in the use of less x-ray dye, and may shorten the procedure time. The ability to strengthen cardiac tissue in critical areas of device implantation will enhance the procedural outcomes and expand treatment options for the patient.

The method of providing internal body landmarks and/or change native tissues is not limited to the heart. Accordingly, the injection device can have applications for marking other organs or tissues in other medical procedures.

Figure 6:
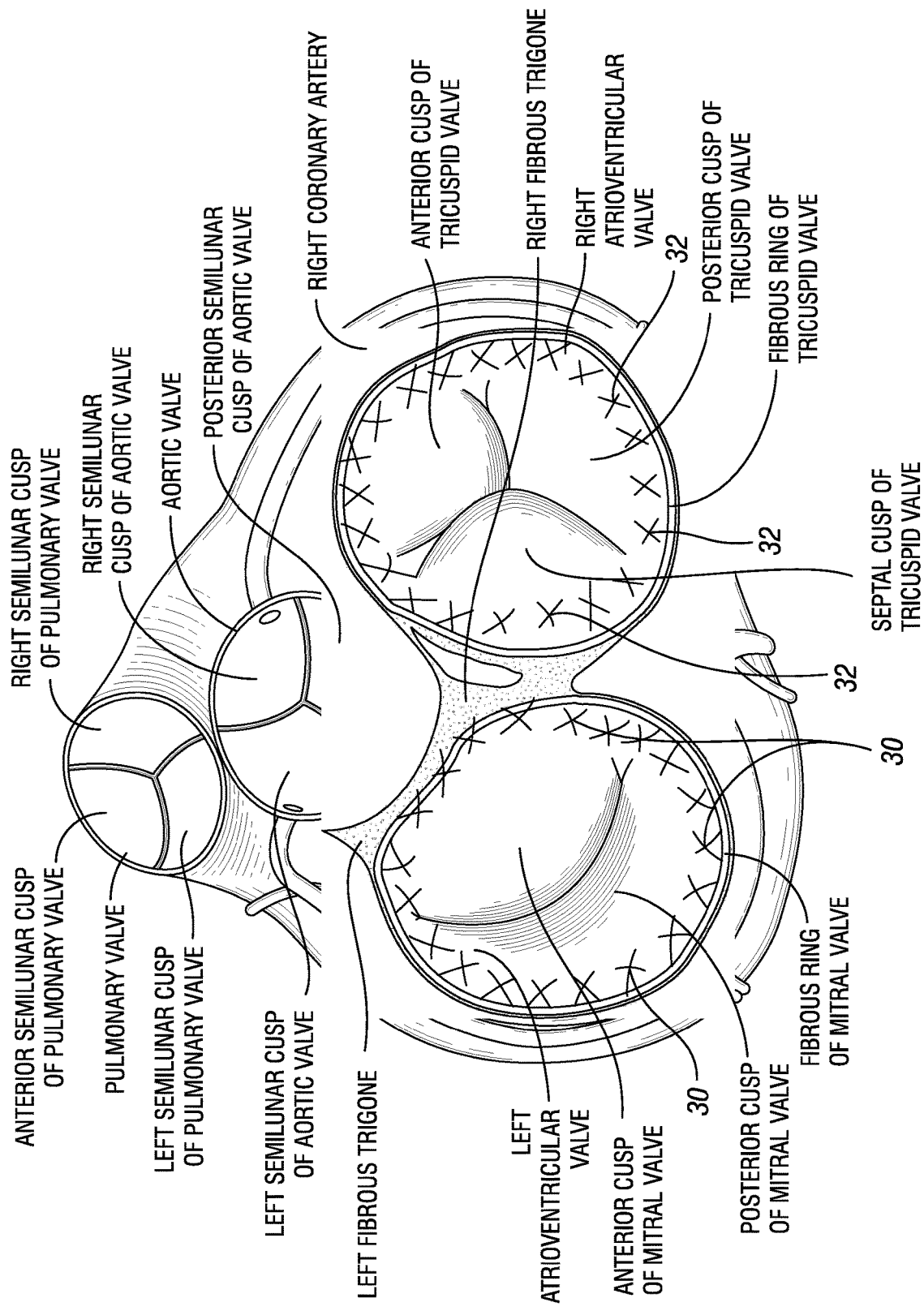
FIG. 6 is a sectional view of the heart of a patient illustrating example locations for injection of a liquid compound capable of solidifying.
Figure 7:
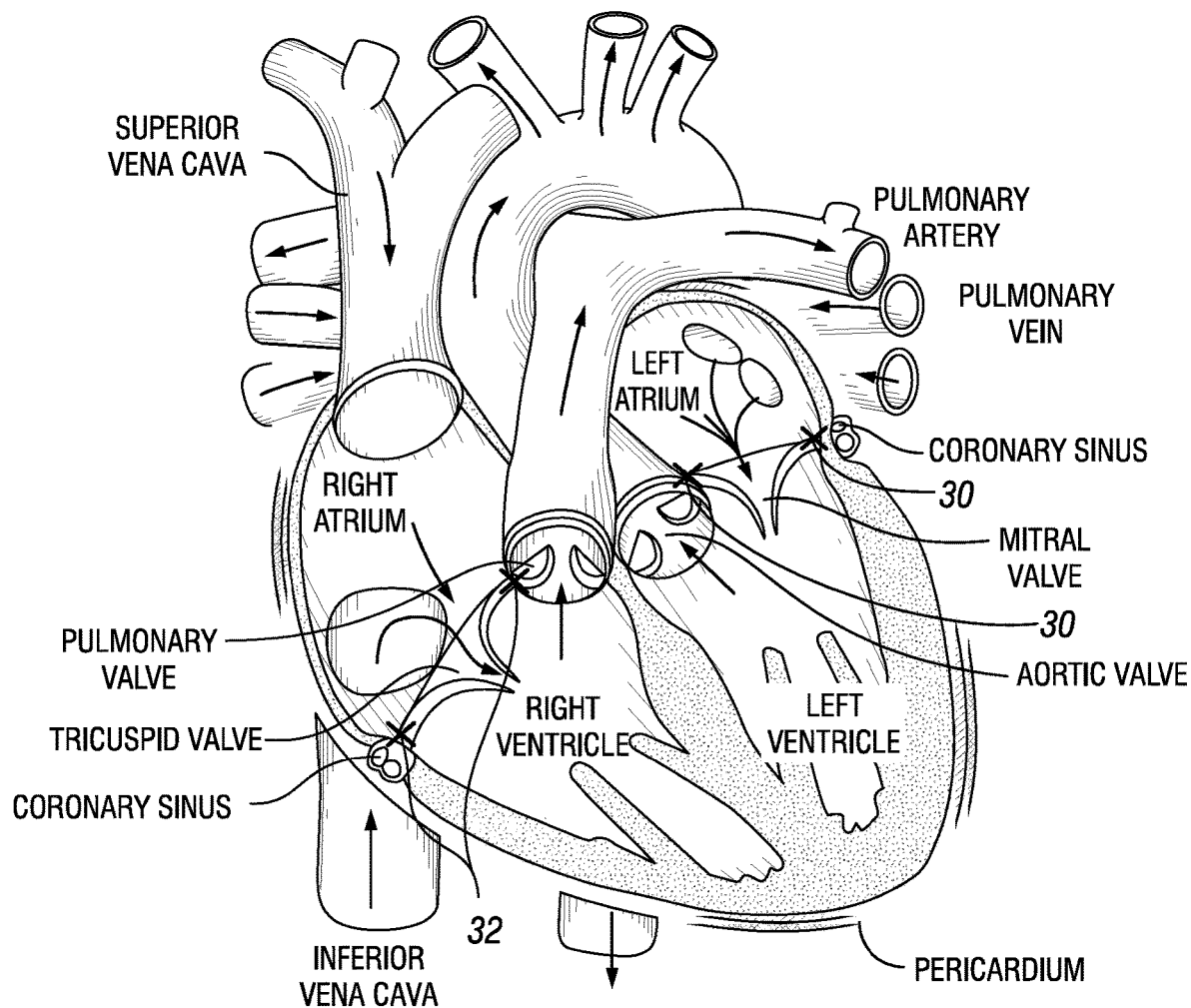
FIG. 7 is another sectional view of the heart of the patient illustrating example locations for injection of a liquid compound capable of solidifying.

FIGS. 6 and 7 describe an internal cardiac annuloplasty procedure that involves reducing the size of the valve annulus, and creating a cardiac annuloplasty ring using the heart's own tissue in order to fix the valve annulus at a reduced size. The procedure can also omit the reduction of the size of the valve annulus and can be used in order to fix the annulus at its present size and prevent further enlargement.

The procedure creates a cardiac annuloplasty ring chemically. An annuloplasty ring that is created chemically using the heart's own tissue may offer a very efficient and cost-effective way of dealing with one of the world's major causes of congestive heart failure.

The internal cardiac annuloplasty procedure can be used for preventing and treating congestive heart failure. Unlike the present valve annular procedures, this procedure creates an annuloplasty ring that is embedded in the heart tissue, and it may not leave a structure entirely external to the heart tissue.

A device similar to that which has been described in FIGS. 1-5 can be used in the internal cardiac annuloplasty procedure. A steerable guide catheter, such as the outer catheter 14 shown in FIG. 5, and an injection catheter having one or more short needles at its end, such as the injection catheter 10 shown in FIGS. 1-3, can be advanced to the atrial side of the valve and the perimeter of the valve at the annulus (area of leaflet insertion). If the mitral valve is the target, a transseptal puncture may be required. The distal tip of the steerable guide catheter can be directed in all four directions. The injection catheter is movable within the steerable guide catheter. Once the steerable guide catheter is positioned above the cardiac valve, the injection catheter is advanced out of the distal end of the steerable guide catheter and pressed against the cardiac tissue. The short, protruding needle(s) at the end of the injection catheter, such as the short needle 18 shown in FIG. 2 or the plurality 24 of short needles shown in FIG. 3, is(are) advanced into the cardiac tissue. As such, the valve annulus can be injected, for example, with a cyanoacrylate compound. The compound may be formed by mixing the cyanoacrylate with a small amount of tungsten or tantalum powder, which may facilitate the radiographic identification of the injected areas. Optionally, the compound may contain ethiodized oil, which is a lipophilic non-ionic iodinated contrast medium.

The preferred locations of injection of the compound inside the tissue around the annulus of the mitral valve 30 or the tricuspid valve 32 are illustrated in FIGS. 6 and 7. In other embodiments, the locations may be more densely or more sparsely spaced than shown. In other embodiments, the locations may be only around the annulus of the mitral valve or only around the annulus of the tricuspid valve. The injections at the preferred locations can be done sequentially, in any order, with the steerable guiding catheter being directed to the next site of injection after each injection. The positioning of the steerable guiding catheter and/or the injection catheter within the heart can be done with the use of x-ray and transesophageal echocardiography imaging.

This injection of the compound may result in almost immediate hardening of the tissue in the area of injection. The hardened tissue can create an internal annuloplasty ring with the result of preventing the size of the valve annulus from increasing.

With the internal cardiac annuloplasty procedure, there may be at least two treatment options for the patients. The first option may comprise injecting and fixing the annulus at its present size to prevent future enlargement of the annulus and the resultant increase in congestive heart failure. The second option may comprise constricting the valve annulus and then injecting and fixing the annulus at the new reduced size.

Temporary constriction of the valve annulus may be accomplished by several different means. One of the means of constricting the annulus can utilize an instrument that is temporarily placed in the coronary sinus. This instrument can be used to constrict the midsection of the heart to reduce the annular sizes. After the injection of the cyanoacrylate and subsequent curing, the instrument is removed from the coronary sinus. For example, the instrument may comprise a specially designed constriction catheter that can be positioned in the coronary sinus with the aid of a guidewire. Once position in the sinus is confirmed by x-ray, a distal balloon on the constriction catheter can be inflated to anchor the device within the coronary sinus. The distal shape of the constriction catheter can then be deformed as desired by a mechanical mechanism similar to the mechanism that controls a steerable guide catheter. When the injection procedure is completed, the balloon is deflated, and the constriction catheter is removed from the coronary sinus. Other means of constricting the annulus may alternatively be used.

The cyanoacrylate compound quickly solidifies and creates a hardened internal ring within the tissue of the valve annulus that fixes the new annular configuration. The cyanoacrylate also induces a subsequent, localized fibrotic reaction that can further strengthen this ring. The process of cyanoacrylate hardening of the cardiac tissue and inducing subsequent fibrosis allows the body to create its own annuloplasty ring. Other compounds besides cyanoacrylate may be used in this internal cardiac procedure to create a hardened internal structure after solidification of the compound (e.g., after curing of the compound), and optionally, to induce subsequent fibrosis.

What is claimed is:

1. A surgical device for injecting a substance into tissue of a patient, comprising:
   an injector device including a mechanism configured to hinder ejection flow of the substance to be injected between successive ejections;
   a tube having a proximal end connected to the injector device and a distal end;
   an outer catheter having a bore sized to allow insertion and movement of the tube, wherein the outer catheter is a steerable guide catheter; and
   one or more needles that protrude from the distal end of the tube,
   wherein the distal end of the tube is sealed around the one or more needles, and
   wherein the injector device contains a mixture of a marking dye and a fluid capable of inducing tissue changes.

2. The surgical device of claim 1, wherein the injector device comprises:
   a barrel for containing the substance to be injected;
   a plunger slidable inside the barrel for applying pressure to the substance being injected; and
   a rod connected to the plunger and extending from the barrel.

3. The surgical device of claim 2, wherein the mechanism to hinder ejection flow of the substance to be injected between successive ejections comprises one or more of a valve and a trigger, the trigger being configured to release a ratchet mechanism used to lock the plunger position.

4. The surgical device of claim 1, wherein the tube has a dual lumen configuration.

5. The surgical device of claim 4, wherein one of the lumens provides passage to a form of energy.

6. The surgical device of claim 5, wherein the form of energy is a laser beam.

7. The surgical device of claim 1, wherein a plurality of needles protrude from the distal end of the tube.

8. The surgical device of claim 1, wherein the steerable guide catheter can deflect a distal segment in four quadrants.

9. The surgical device of claim 1 wherein the marking dye includes a radiographic marker.

10. The surgical device of claim 1 wherein the fluid is capable of inducing fibrosis of a cardiac tissue.

11. A surgical device for injecting a substance into tissue of a patient, comprising:
- an injector device including a mechanism configured to hinder ejection flow of the substance to be injected between successive ejections;
- a tube having a proximal end connected to the injector device and a distal end;
- an outer catheter having a bore sized to allow insertion and movement of the tube, wherein the outer catheter is a steerable guide catheter; and
- one or more needles that protrude from the distal end of the tube,
- wherein the distal end of the tube is sealed around the one or more needles, and
- wherein the outer catheter further includes a hemostatic valve positioned at a proximal end of the outer catheter, wherein the hemostatic valve is configured to allow insertion and movement of the tube.

12. The surgical device of claim 11, wherein the injector device contains a marking dye capable of being seen by x-ray or echocardiography.

13. The surgical device of claim 12 wherein the marking dye is iodine-based.

14. The surgical device of claim 12 wherein the marking dye includes tungsten, tantalum, or both.

15. The surgical device of claim 11 wherein the injector device includes a compound capable of inducing fibrotic tissue changes.

16. The surgical device of claim 15 wherein the compound includes an irritant.

17. The surgical device of claim 15 wherein the compound includes a fibroblast growth factor.

18. The surgical device of claim 15 wherein the compound includes cyanoacrylate.

19. The surgical device of claim 11 wherein the injector device contains a liquid compound that is capable of solidifying.

20. The surgical device of claim 19 wherein the liquid compound includes cyanoacrylate.

21. The surgical device of claim 11 wherein the injector device contains a mixture of a marking dye and a fluid capable of inducing tissue changes.

22. A surgical device for injecting a substance into tissue of a patient, comprising:
- an injector device including a mechanism configured to hinder ejection flow of the substance to be injected between successive ejections;
- a tube having a proximal end connected to the injector device and a distal end;
- an outer catheter having a bore sized to allow insertion and movement of the tube, wherein the outer catheter is a steerable guide catheter; and
- one or more needles that protrude from the distal end of the tube,
- wherein the distal end of the tube is sealed around the one or more needles, and
- wherein the outer catheter further includes a side port closable with a valve.

23. The surgical device of claim 22, wherein the injector device contains a mixture of a marking dye and a fluid capable of inducing tissue changes.

* * * * *